United States Patent [19]

Gruenberg

[11] Patent Number: 5,690,646
[45] Date of Patent: Nov. 25, 1997

[54] UMBILICAL CORD BLOOD COLLECTION DEVICE AND METHOD

[76] Inventor: Lisa J. Gruenberg, 74 Claypit Hill Rd., Wayland, Mass. 01778

[21] Appl. No.: 705,784

[22] Filed: Aug. 30, 1996

[51] Int. Cl.⁶ .............................. A61B 17/42; A61M 1/00
[52] U.S. Cl. .......................... 606/120; 606/157; 604/317; 128/760
[58] Field of Search ........................ 606/120, 142, 606/151, 157, 158, 174; 128/760, 763; 604/4, 317

[56] References Cited

U.S. PATENT DOCUMENTS

| | | | |
|---|---|---|---|
| 5,011,487 | 4/1991 | Shichman | 606/158 |
| 5,057,118 | 10/1991 | Picha | 606/158 |
| 5,190,556 | 3/1993 | Hessel | 606/120 |
| 5,304,188 | 4/1994 | Marogil | 606/157 |
| 5,342,328 | 8/1994 | Grossman et al. | 604/317 |
| 5,372,581 | 12/1994 | Anderson | 604/32 |
| 5,415,665 | 5/1995 | Hessel et al. | 606/120 |
| 5,462,555 | 10/1995 | Bolanos et al. | 606/120 |
| 5,520,699 | 5/1996 | Hessel et al. | 606/120 |
| 5,575,795 | 11/1996 | Anderson | 606/157 |

*Primary Examiner*—John G. Weiss
*Assistant Examiner*—David J. Cho
*Attorney, Agent, or Firm*—Fish & Richardson P.C.

[57] ABSTRACT

An umbilical cord blood collection device includes a base defining a collection surface for receiving and supporting a segment of an umbilical cord, in communication with a placenta, from which blood is to be collected. The base, in at least a region including the collection surface, is resistant to penetration by a blood collection needle. A clamp is mounted at a first end region of the collection surface for clamping engagement across the umbilical cord supported upon the collection surface. A securement strap is disposed in an opposite, second end region of the collection surface for securing engagement with the umbilical cord. A malleable arm has a first end mounted to the base and a second, free end supporting a blood collection needle. A method for collection of umbilical cord blood is also described.

17 Claims, 4 Drawing Sheets

UMBILICAL CORD BLOOD COLLECTION DEVICE AND METHOD

The invention relates to device for collection of umbilical cord blood.

BACKGROUND OF THE INVENTION

It has become known that the blood present in the umbilical cord at birth has considerable potential curative value, e.g., for use in bone marrow replacement procedures for treatment of cancer and immunodeficiency disorders. In the past, this volume of blood (typically about 1–2 pints) has typically been discarded with the placenta. However, commercial services now offer to arrange for collection and storage of the blood for personal or family use. NIH (National Institutes of Health) has now been funding research with the intent of establishing donor blood banks throughout the country.

One recognized concern in widespread collection of blood from the umbilical cord is the problem of accidental needle sticks to birth room staff. These needle sticks can occur during insertion of the collection needle into a blood vessel of the umbilical cord while it is held in the person's hand.

SUMMARY OF THE INVENTION

According to one aspect of the invention, an umbilical cord blood collection device comprises a base defining a collection surface for receiving and supporting a segment of an umbilical cord, in communication with a placenta, from which blood is to be collected, the base, in at least a region including the collection surface, being resistant to penetration by a blood collection needle; a clamp mounted at a first end region of the collection surface for clamping engagement across the umbilical cord supported upon the collection surface; a securement strap disposed in a second end region of the collection surface, opposite the first end region, for securing engagement with the umbilical cord; and a malleable arm having a first end mounted to the base and a second, free end supporting a blood collection needle.

Preferred embodiments of this aspect of the invention may include one or more of the following additional features. The base is sized to fit within a person's hand, and/or the base defines an under surface region adapted to support the device in stable, rest position upon a flat surface. The base further comprises at least a pair of raised side walls disposed at opposite side edge regions of the collection surface to resist slippage of the blood collection needle from the collection surface.

Preferably, the raised side walls are resistant to penetration by the blood collection needle. Preferably also, at least one raised side wall has an outer surface with protuberances to resist slipping from a user's hand. The blood collection needle is in communication with a blood collection tubing, and the base further comprises a blood collection tubing attachment member for releasable securement of the blood collection tubing to the base, thereby to resist dislodgement of the blood collection needle. Preferably, the blood collection tubing attachment member comprises a notch defined in a wall of the base. The securement strap comprises a securement sheet of transparent material disposed to extend over at least a portion of the collection surface, with the umbilical cord disposed between the securement sheet and the collection surface, the securement sheet being penetrable by the blood collection needle. The umbilical cord blood collection device further comprises a cover defining a frame upon which the securement sheet of transparent material is mounted, the cover having a first position in which the collection surface is exposed and a second position in which the securement sheet is disposed to extend over at least a portion of the collection surface. Preferably, the frame further defines at least a portion of the clamp. Preferably also, the cover is hingedly mounted to the base.

According to another aspect of the invention, an method for collection of umbilical cord blood comprises the steps of: providing an umbilical cord blood collection device comprising a base defining a collection surface for receiving and supporting a segment of an umbilical cord, in communication with a placenta, from which blood is to be collected, the base, in at least a region including the collection surface, being resistant to penetration by a blood collection needle; a clamp mounted at a first end region of the collection surface for clamping engagement across the umbilical cord supported upon the collection surface; a securement strap disposed in a second end region of the collection surface, opposite the first end region, for securing engagement with the umbilical cord; and a malleable arm having a first end mounted to the base and a second, free end supporting a blood collection needle; placing a segment of the umbilical cord in communication with a placenta from which blood is to be collected upon the collection surface; engaging the clamp upon the umbilical cord; engaging the securement strap upon the umbilical cord at a position relatively closer to the placenta; with the base held in one hand or resting upon a surface, manipulating the malleable arm to a position for insertion of the blood collection needle into a vessel of the umbilical cord; inserting the blood collection needle into the vessel for collection of blood; and upon completion of blood collection, disposing of the umbilical cord blood collection device.

Preferred embodiments of this aspect of the invention may include one or more of the following additional features. The method comprises the further step of securing a blood collection tubing in communication with the blood collection needle to the base. The securement strap of the umbilical cord blood collection device comprises a securement sheet of transparent material disposed to extend over at least a portion of the collection surface, with the umbilical cord disposed between the securement sheet and the collection surface, and the method comprises the further step of inserting the blood collection needle through the securement sheet into the vessel. The umbilical cord blood collection device further includes a cover defining a frame upon which the securement sheet of transparent material is mounted, and the method comprises the further steps of: placing the cover in a first position in which the collection surface is exposed, and thereafter proceeding with the step of placing a segment of the umbilical cord in communication with a placenta from which blood is to be collected upon the collection surface; and placing the cover is a second position in which the securement sheet is disposed to extend over at least a portion of the collection surface with the umbilical cord disposed thereupon. Preferably, the method comprises the further step, upon completion of blood collection, of severing the umbilical cord from the placenta and disposing of the device and remaining cord segment secured thereupon as a unit.

These and other features and advantages of the invention will be apparent from the following description of a presently preferred embodiment, and from the claims.

DESCRIPTION OF THE PREFERRED EMBODIMENTS

Figure 1:
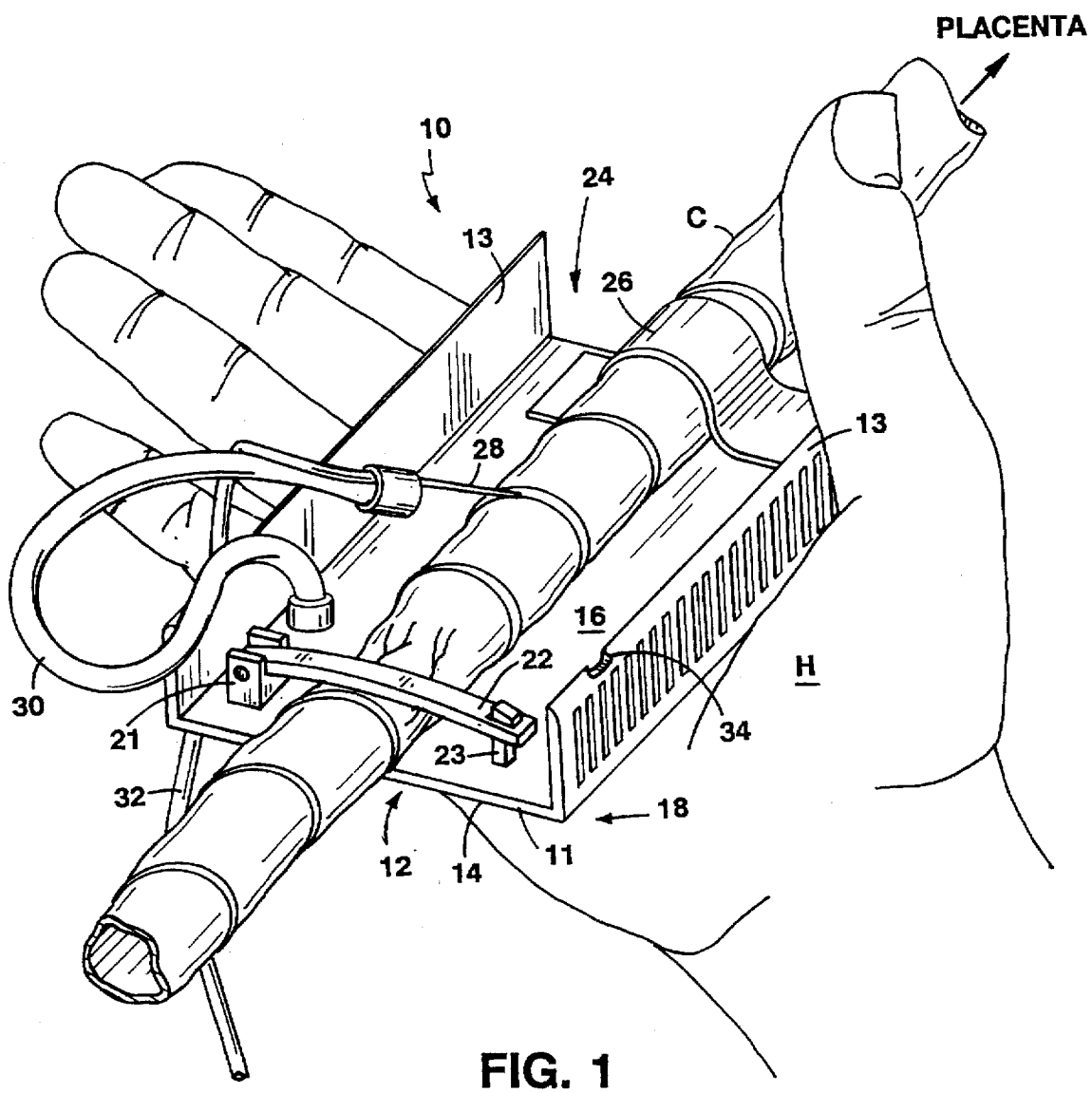
FIG. 1 is a prospective view an umbilical cord blood collection device of the invention held in the hand of birth room staff person.
Figure 2:
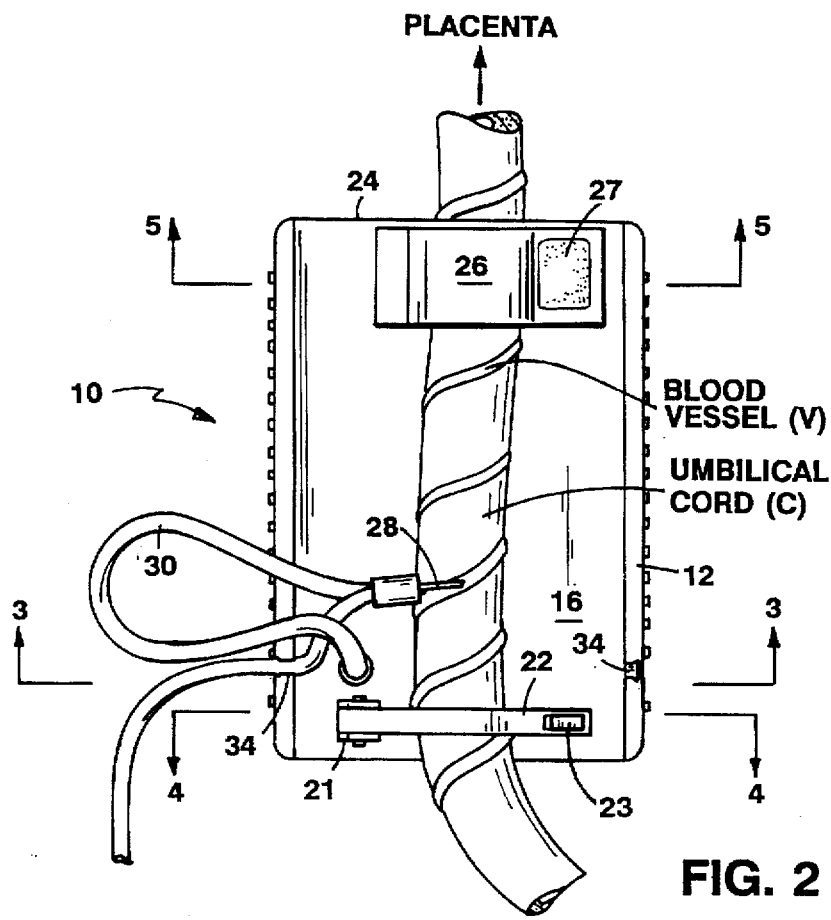
FIG. 2 is a top plan view of the umbilical cord blood collection device of FIG. 1.
Figure 3:
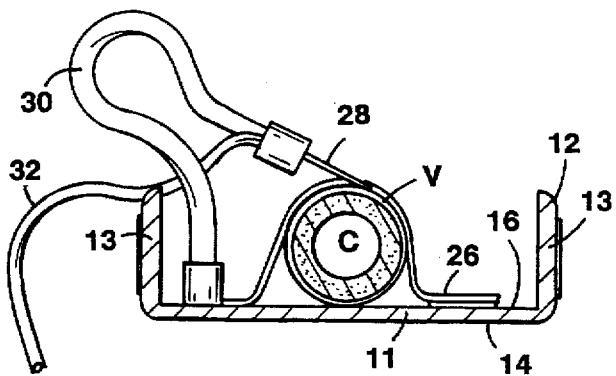
FIG. 3 is an end view of the umbilical cord blood collection device taken at the line 3—3 of FIG. 1.
Figure 4:
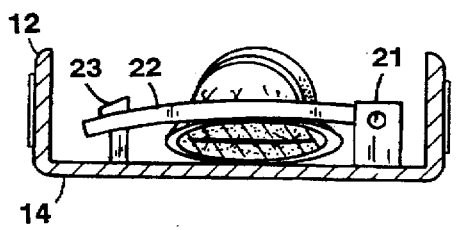
FIG. 4 is an end section view of the umbilical cord blood collection device taken at the line 4—4 of FIG. 1.
Figure 5:
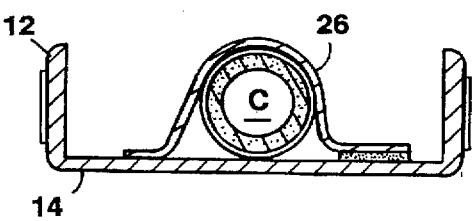
FIG. 5 is an end section view of the umbilical cord blood collection device taken at the line 5—5 of FIG. 1.
Figure 6:
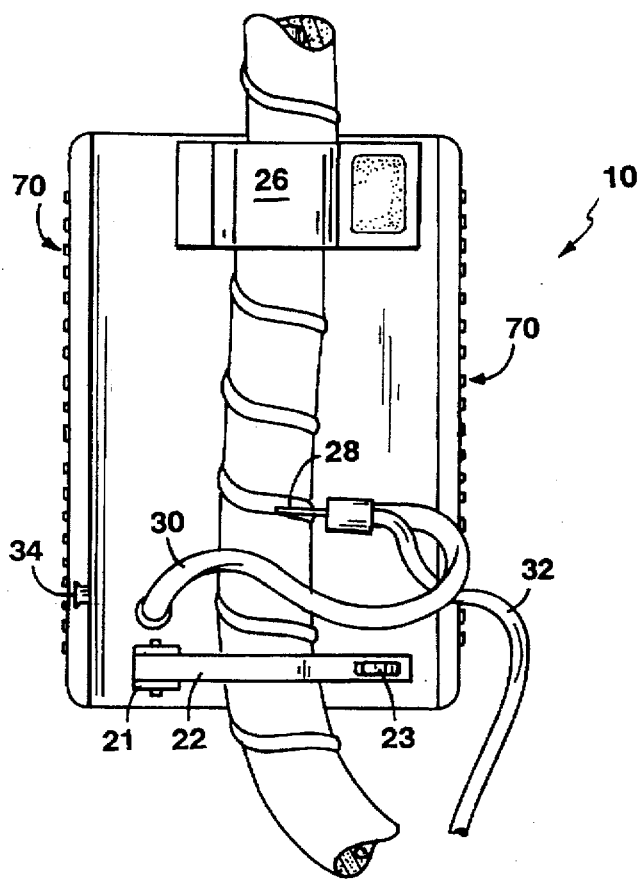
FIG. 6 is another top plan view of the umbilical cord blood collection device of FIG. 1, showing the umbilical cord blood vessel at a different orientation.

Referring to FIGS. 1–6, an umbilical cord blood collection device 10 of the invention consists of a base tray 12, with a bottom wall 11 and side walls 13 formed, e.g., of a hard, needle-penetration-resistant material, such as a suitable plastic.

The base tray is sized to fit in the palm of a birth room staff person's hand, H. It also has a generally flat lower surface 14 to alternatively allow the device to be placed, e.g., on the operating table or other flat surface during use.

Mounted upon an upper, collection surface 16 of the base tray 12, at a first end 18, is a clamp 20, e.g. with a an arm 21 pivotally mounted to post 22, and having a free end engaged (e.g. by camming action) over hooked post 23, for clamping flow through the umbilical cord. At an opposite, second end 24 of the collection surface 16, there is mounted a strap 26 or other element for holding the umbilical cord, C, in place without restricting blood flow from the placenta. In the embodiment shown, securement strap 26 has a first end attached upon the collection surface 16 and a second, free end secured to the collection surface after the umbilical cord is in place, e.g. upon an exposed adhesive area 27.

A large bore collection needle 28 is mounted to the base tray 12 by a malleable arm 30, e.g. a metal wire embedded in plastic, having a first end attached to the base and a second, free end supporting the needle 28. The malleable nature of the arm 30 allows the needle 28 to be positioned and inserted from the left (FIG. 2) or from the right (FIG. 6), to accommodate either spiral (i.e. helix) direction of the blood vessel, V, about the umbilical cord. The arm 30 is also selected to be sufficiently stiff to maintain the position of the needle 28 inserted into the vessel during the blood collection procedure. A blood collection tubing 32 connects the needle bore to a collection bag (not shown) for collection of blood. In one preferred embodiment, the tubing is releasably engaged in a notch 34 defined by the base side wall 13 to resist dislodgement of the blood collection needle, e.g. due to tension applied to the tubing.

The umbilical blood collection device 10 is provided in sterile condition. After birth of a child, before the placenta is removed from the mother, the umbilical cord, C, is placed upon the collection surface 16 of the base tray 12, and the hinged arm 22 of the clamp 20 is secured across the cord to obstruct blood flow from the free end of the cord. (To ensure sterile collection of the blood, a segment of the umbilical cord can be prepared with a standard betadyne prep before being placed on the base tray.) The strap 26 is placed across the cord to secure the cord in position upon the base tray 12. Then, with the base tray 12 either held in the birth room staff person's hand (FIG. 1) or placed upon a flat surface (FIG. 2), the sterile needle 28 mounted upon malleable arm 30 is inserted into a vessel, V, of the umbilical cord to begin flow of blood through the tubing 32 (which may be secured to the base by engagement in notch 34) to the collection bag. The staff person is thus protected from an accidental stick by needle-penetration-resistant material of the base tray 12.

When the blood collection process is completed, the needle 28 may be cut off and discarded in a sharps container according to usual procedures, or the device may be discarded as a unit, e.g. with a segment of the umbilical cord still in place.

Figure 7:
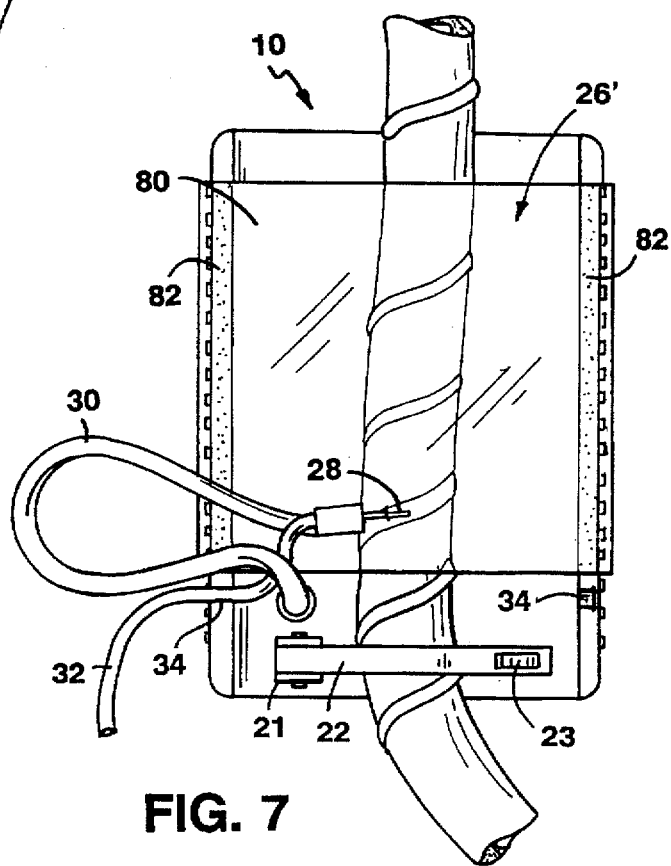
FIG. 7 is an end view of another embodiment of an umbilical cord blood collection device of the invention with a transparent sheet for securement of the umbilical cord.

Referring to FIG. 7, in another embodiment, a device 10' of the invention has a securement strap 26' consisting of a transparent plastic sheet 80, which may be impregnated with a sterilizing medium, e.g. similar to sterilizing drapes used in surgery. The sheet 80 is placed over the umbilical cord, C, and secured upon the base 12, e.g. by areas 82 of sterile contact adhesive. The needle 28 is then inserted into the umbilical cord, C, through the plastic sheet 80.

Figure 8:
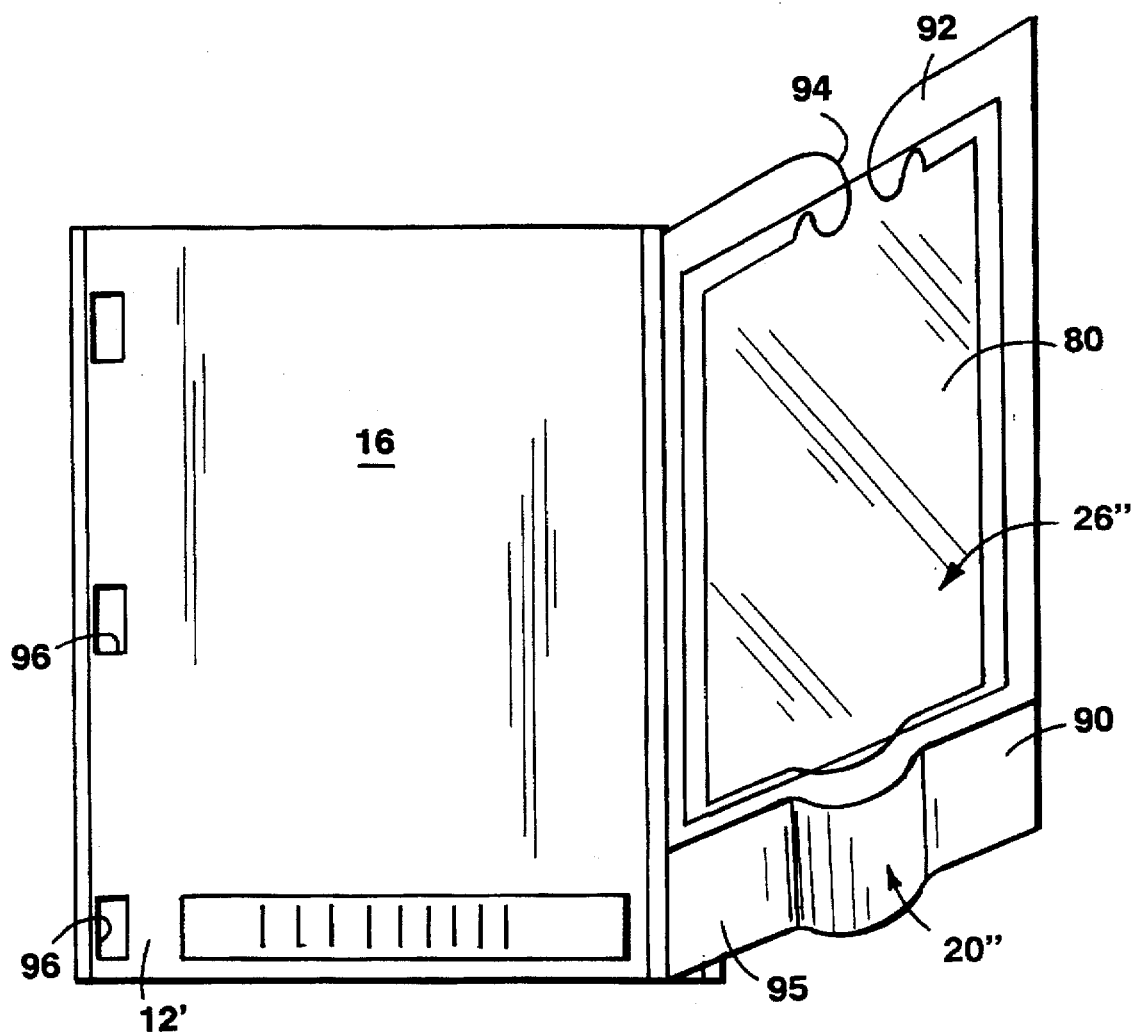
FIG. 8 is a similar end view of another embodiment of an umbilical cord blood collection device of the invention with a hinged cover for securement of the umbilical cord.

Referring to FIG. 8, in still another embodiment, the transparent plastic sheet 80, forming securement strap 26", is suspended from a frame 90 attached to the base 12'. The top edge 92 of the frame 90 defines an aperture 94 for passage of the umbilical cord, C, without restriction of blood flow. The lower edge 95 of the frame 90 defines the upper portion of a clamp 20". In the embodiment shown, the frame 90 is hinged to the base 12' along side edge of the surface 16, to be secured by snaps 96 along the opposite side edge. Alternatively, a separable frame 90 may be provided and secured to the base by snaps or other suitable fasteners.

In the embodiments of FIGS. 7 and 8, when the blood collection process is completed, the film 80 or frame 90 may be left in place, with the remnant section of the cord remaining on the base tray 12 and the needle 28 still in place. The entire device can then be handled as a unit for disposal with other medical contaminated waste.

Other embodiments are within the following claims. For example, referring again to FIG. 6, the base 12 may define enhanced side gripping surfaces 70, e.g. with ridges or grooves. Other methods for releasable securement of the tubing 32 to the base 12 are also contemplated, e.g. a strap or sterile contact adhesive area may be provided.

What is claimed is:

1. An umbilical cord blood collection device comprising:

a base defining a collection surface for receiving and supporting a segment of an umbilical cord, in communication with a placenta, from which blood is to be collected, said base, in at least a region including said collection surface, being resistant to penetration by a blood collection needle;

a clamp mounted at a first end region of said collection surface for clamping engagement across the umbilical cord supported upon said collection surface;

a securement strap disposed in a second end region of said collection surface, opposite said first end region, for securing engagement with the umbilical cord; and a malleable arm having a first end mounted to said base and a second, free end supporting a blood collection needle.

2. The umbilical cord blood collection device of claim 1, wherein said base is sized to fit within a person's hand.

3. The umbilical cord blood collection device of claim 1 or 2, wherein said base defines an under surface region adapted to support said device in stable, rest position upon a flat surface.

4. The umbilical cord blood collection device of claim 1, wherein said base further comprises at least a pair of raised side walls disposed at opposite side edge regions of said collection surface to resist slippage of said blood collection needle from said collection surface.

5. The umbilical cord blood collection device of claim 4, wherein said raised side walls are resistant to penetration by said blood collection needle.

6. The umbilical cord blood collection device of claim 4, wherein at least one said raised side wall has an outer surface with protuberances to resist slipping from a user's hand.

7. The umbilical cord blood collection device of claim 1, wherein said blood collection needle is in communication with a blood collection tubing, and said base further comprises a blood collection tubing attachment member for releasable securement of the blood collection tubing to said base, thereby to resist dislodgement of said blood collection needle.

8. The umbilical cord blood collection device of claim 7, wherein said blood collection tubing attachment member comprises a notch defined in a wall of said base.

9. The umbilical cord blood collection device of claim 1, wherein said securement strap comprises a securement sheet of transparent material disposed to extend over at least a portion of said collection surface, with the umbilical cord disposed between said securement sheet and said collection surface, said securement sheet being penetrable by said blood collection needle.

10. The umbilical cord blood collection device of claim 9, further comprising a cover defining a frame upon which said securement sheet of transparent material is mounted, said cover having a first position in which said collection surface is exposed and a second position in which said securement sheet is disposed to extend over at least a portion of said collection surface.

11. The umbilical cord blood collection device of claim 10, wherein said frame defines at least a portion of said clamp.

12. The umbilical cord blood collection device of claim 10 or 11, wherein said cover is hingedly mounted to said base.

13. A method for collection of umbilical cord blood, said method comprising the steps of:

providing an umbilical cord blood collection device comprising a base defining a collection surface for receiving and supporting a segment of an umbilical cord, in communication with a placenta, from which blood is to be collected, the base, in at least a region including the collection surface, being resistant to penetration by a blood collection needle; a clamp mounted at a first end region of the collection surface for clamping engagement across the umbilical cord supported upon the collection surface; a securement strap disposed in a second end region of the collection surface, opposite the first end region, for securing engagement with the umbilical cord; and a malleable arm having a first end mounted to the base and a second, free end supporting a blood collection needle;

placing a segment of the umbilical cord in communication with a placenta from which blood is to be collected upon the collection surface;

engaging the clamp upon the umbilical cord;

engaging the securement strap upon the umbilical cord at a position relatively closer to the placenta;

with the base held in one hand or resting upon a surface, manipulating the malleable arm to a position for insertion of the blood collection needle into a vessel of the umbilical cord;

inserting the blood collection needle into the vessel for collection of blood; and upon completion of blood collection, disposing of the umbilical cord blood collection device.

14. The method of claim 13, comprising the further step of securing a blood collection tubing in communication with the blood collection needle to the base.

15. The method of claim 13, wherein the securement strap of the umbilical cord blood collection device comprises a securement sheet of transparent material disposed to extend over at least a portion of the collection surface, with the umbilical cord disposed between the securement sheet and the collection surface, said method comprising the further step of inserting the blood collection needle through the securement sheet into the vessel.

16. The method of claim 15, wherein the umbilical cord blood collection device further includes a cover defining a frame upon which the securement sheet of transparent material is mounted, the method comprising the further steps of:

placing the cover in a first position in which the collection surface is exposed, and thereafter proceeding with the step of placing a segment of the umbilical cord in communication with a placenta from which blood is to be collected upon the collection surface; and placing the cover is a second position in which the securement sheet is disposed to extend over at least a portion of the collection surface with the umbilical cord disposed thereupon.

17. The method of claim 13, 15 or 16, comprising the further step, upon completion of blood collection, of severing the umbilical cord from the placenta and disposing of the device and remaining cord segment secured thereupon as a unit.

* * * * *